United States Patent [19]
Doyle

[11] Patent Number: 6,146,426
[45] Date of Patent: *Nov. 14, 2000

[54] PROSTHETIC POLYETHYLENE BEARING HAVING ENHANCED WEAR PROPERTIES

[75] Inventor: Christina Doyle, Cranleigh, United Kingdom

[73] Assignee: Howmedica Interntional Inc., Ireland

[*] Notice: This patent issued on a continued prosecution application filed under 37 CFR 1.53(d), and is subject to the twenty year patent term provisions of 35 U.S.C. 154(a)(2).

[21] Appl. No.: 08/742,540

[22] Filed: Nov. 1, 1996

[30] Foreign Application Priority Data

Nov. 2, 1995 [GB] United Kingdom .................... 9522478

[51] Int. Cl.⁷ ........................................................ A61F 2/30
[52] U.S. Cl. ........................................................ 623/23.58
[58] Field of Search ............................. 623/23.51, 23.58, 623/23.59

[56] References Cited

U.S. PATENT DOCUMENTS

| | | | |
|---|---|---|---|
| 4,655,769 | 4/1987 | Zachariades | 623/1 |
| 4,747,990 | 5/1988 | Gaussens et al. | 264/322 |
| 4,801,419 | 1/1989 | Ward et al. | 264/288 |
| 5,030,402 | 7/1991 | Zachariades | 264/138 |
| 5,609,638 | 3/1997 | Price et al. | 623/18 |

FOREIGN PATENT DOCUMENTS

| | | |
|---|---|---|
| 0371769A2 | 6/1990 | European Pat. Off. . |
| 4006714 A1 | 9/1990 | Germany ................................. 623/20 |
| 2060469B | 9/1983 | United Kingdom . |
| 2156733B | 10/1987 | United Kingdom . |
| 2225551B | 2/1993 | United Kingdom . |

OTHER PUBLICATIONS

"Elastic Moduli of Highly Oriented Polyoxymethylene" by C.L. Choy et al, in Polymer Engineering & Science, Nov. 1983, vol. 26, #16 pp. 910–922.

*Primary Examiner*—David H. Willse
*Attorney, Agent, or Firm*—Lerner, David, Littenberg, Krumholz & Mentlik, LLP

[57] ABSTRACT

A prosthetic bearing element having a bearing surface is made from an ultra-high molecular weight polyethylene with a molecular weight greater than 1,000,000 with a multi-axially molecular orientation. From tests which have been applied to such material, it has been found that the wear rate is lowered and preferably the direction of one of said axial molecular orientations extends parallel with or along the length of the bearing surface.

11 Claims, 9 Drawing Sheets

MECHANICAL PROPERTIES (BATCH 1) MEAN + SE

PROSTHETIC POLYETHYLENE BEARING HAVING ENHANCED WEAR PROPERTIES

BACKGROUND OF THE INVENTION

1. Field of the Invention

This invention relates to a prosthetic bearing element and to an implant incorporating such an element.

2. Description of the Prior Art

Prosthetic bearing elements are employed in many prosthetic implants and can be made from various materials, for example, polyethylene or nylon, provided the bearing material is compatible with the human body.

Such elements are usually held in a metal housing which carries the load although, in certain circumstances, they may be used by themselves, for example as an acetabular cup. Typical use of such elements is in knee prostheses where they are used on a tibial tray and cooperate with a femoral component. They are also used in patella constructions and act between the femoral and patella components. Yet another use, as referred to above, is as bearing cups in hip implants.

A favored material, at the present time, is polyethylene, particularly ultra high molecular weight polyethylene (UHMWPE) with a molecular weight greater than 1,000,000. It has been found however, that even this material wears and the present Applicants have therefore carried out research into the possibility of treating the material to improve the wear qualities. It has been found that a multi-axially molecular orientation in the material provides such qualities.

SUMMARY OF THE INVENTION

According to the present invention therefore, a prosthetic bearing element having a bearing surface is made form an ultra-high molecular weight polyethylene with a molecular weight greater than 1,000,000 with a multi-axially molecular orientation. From tests which have been applied to such material, it has been found that the wear rate is lowered and preferably the direction of one of said axial molecular orientations extends parallel with or along the length of the bearing surface.

Alternatively, the direction of one of said axial molecular orientations may extend parallel with or across the width of said bearing surface. It can therefore be arranged that there are orientations extending across and along the surface which may or may not be at right angles to each other.

In yet another configuration, the axial molecular orientations may extend towards the bearing surface and may be combined with orientations in other directions, for example, parallel with or along the length and/or parallel with or across the width of the bearing surface. The invention also includes a prosthetic implant incorporating a prosthetic bearing element as set forth above.

The material from which the bearing element is formed can be provided by subjecting a work piece made from UHMWPE with a molecular weight greater than 1,000,000 to solid phase deformation in at least two directions to cause a preferred multi-axially orientation, said deformation in at least two directions, having a deformation ratio of 1.3 to 1.9. The preferred deformation ratios in each direction are 1.5 to 1.6.

The ultra-high molecular weight polyethylene preferably has a molecular weight greater than 4,000,000.

The first deformation can be performed in a lengthwise direction of the work piece and a second deformation preformed in a substantially transverse direction thereto. The second deformation ratio can be greater than the first. In a preferred method the work piece is hollow and is passed over a former of increasing cross-sectional area, the second deformation taking place in a hoop direction.

The hollow work piece can be passed over the former without applying external force. In another method, the work piece is solid and can be square or of rectangular cross-section transverse to its length. In another method, the work piece can be drawn through a die and/or over a former. Alternatively, the work piece can be pressed through the die and/or over the former.

These and other objects and advantages of the present invention will become apparent from the following description of the accompanying drawings, which disclose several embodiments of the invention. It is to be understood that the drawings are to be used for the purposes of illustration only and not as a definition of the invention.

BRIEF DESCRIPTION OF THE DRAWINGS

In the drawings, wherein similar reference characters denote similar elements throughout the several views.

DESCRIPTION OF THE PREFERRED EMBODIMENT

Figure 1:
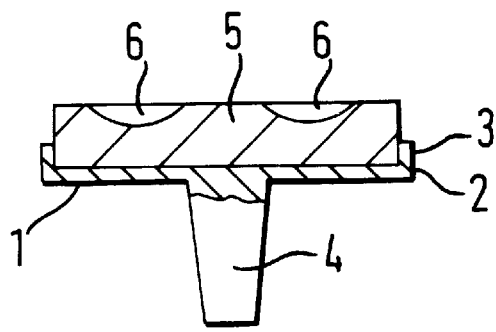
FIG. 1 is a part cross-sectional front elevation of a tibial tray incorporating the invention.
Figure 2:
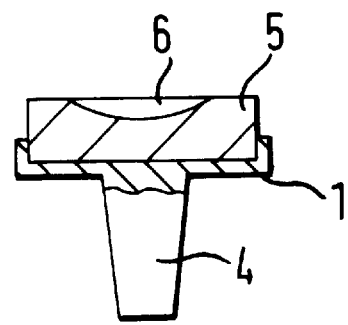
FIG. 2 is a part cross-sectional end elevation of the tray shown in FIG. 1.

FIGS. 1 and 2 show a typical tibial tray for use in a prosthetic implant. The tray comprises a base portion 1, the outer circumference 2 of which is provided with an upstanding lip 3. A spigot 4 extends downwardly from the base 1 to provide attachment to the bone in which it is inserted. The base 1 carries a bearing element 5 which has spaced apart indentations to accept the condyles of the femoral implant (not shown). Tibial trays of this kind are well known in themselves and the construction will not therefore be described further.

According to the present invention, the bearing element 5 is made from ultra high molecular weight polyethylene (UHMWPE) with a molecular weight greater than 1,000,000 and with a multi-axially molecular orientation.

Figure 3:
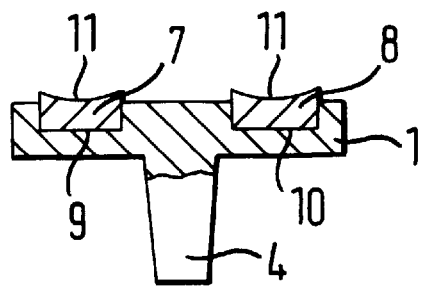
FIG. 3 is a part cross-sectional front elevation of an alternative construction of an alternative construction of a tibial tray incorporating the invention.

FIG. 3 shows an alternative form of tibial tray and the same reference numerals are used to indicate similar parts, but in this construction the base 1 is provided with two separate bearing elements 7 and 8 which are located in recesses 9 and 10. Once again, the bearing elements, each of which has a bearing surface 11, are made from an UHMWPE with a molecular weight greater than 1,000,000 with a multi-axially molecular orientation.

The direction of one of said axial molecular orientations extends parallel with or along the length of the bearing surface, thus, it could extend in a substantially horizontal direction and along the length of the indentation 6 or bearing surfaces 11 along a substantially medio lateral plane. A second molecular orientation may extend at right angles thereto, again, substantially horizontal, or it could extend vertically through the bearing element. Again, a combination of various directions can be used.

Figure 4:
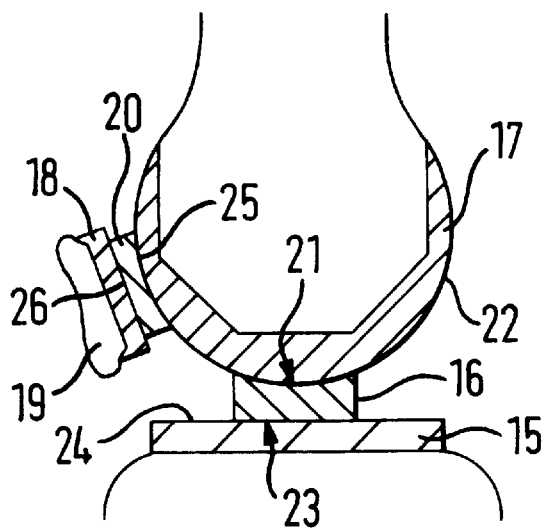
FIG. 4 is a cross-sectional side elevation of a knee joint prosthesis incorporating the invention.

FIG. 4 shows another knee prosthesis, but in this arrangement a tray 15 is provided on the tibia on which is carried a pair of sliding meniscal bearing elements 16. The upper surface of the element 16 is engaged by a femoral implant 17 on which is also carried a patella implant 18 having a metal backing which engages the patella remnant 19. A patella bearing element 20 is arranged between the metal backing and the femoral implant 17.

As will be seen, the bearing elements 16 each have a proximal bearing surface 21 which engages the bearing surface 22 on the femoral implant 19 and further bearing surfaces 23 which engage bearing surfaces 24 on the tray 15. The patella element 20 has a bearing surface 25 which engages the bearing surface 22 on the femoral implant 14 and a further bearing surface 26 which engages the metallic backing.

As described with regard to FIGS. 1, 2 and 3, the bearing elements 16 and 20 are made from an UHMWPE with a molecular weight greater than 1,000,000 with a multi-axially molecular orientation. The orientations can be as described with regard to FIGS. 1, 2 and 3.

Figure 5:
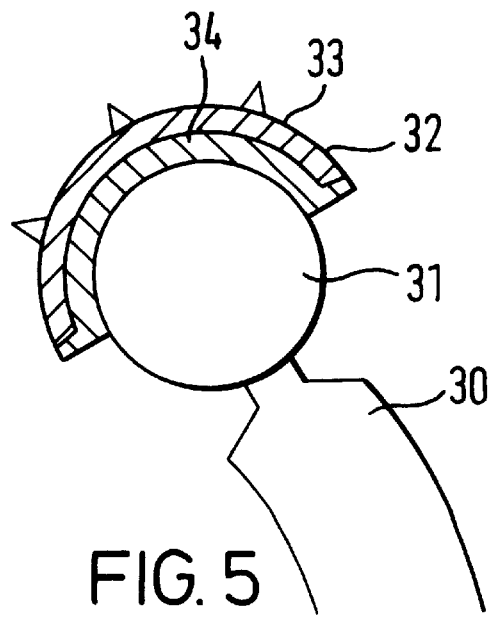
FIG. 5 is a part cross-sectional side elevation of a prosthetic hip joint incorporating the invention.

FIG. 5 shows a hip prosthesis which comprises a femoral insert 30 provided with the usual ball 31. The ball seats in a hip cup 32 which comprises a metallic backing 33 designed for location by any convenient means, for example, cement or mechanical means to the pelvis and which carries a bearing element in the form of a liner 34.

The liner 34 is made from an UHMWPE with a molecular weight greater than 1,000,000 and the multi-axially molecular orientation in the liner 34 and can again be in any way desired and as referred to with regard to FIGS. 1, 2 and 3. It has been found that a preferred molecular weight is greater than 4,000,000.

There are various ways of treating UHMWPE to provide the biaxial orientation and some will now be described with reference to FIGS. 6 to 13. The method is focused on biaxial orientation of UHMWPE to enhance its properties in at least two directions, and establish conditions where the strain energy to failure of the modified material is maintained and that proof of yield stress of the material is increased.

Figure 6:
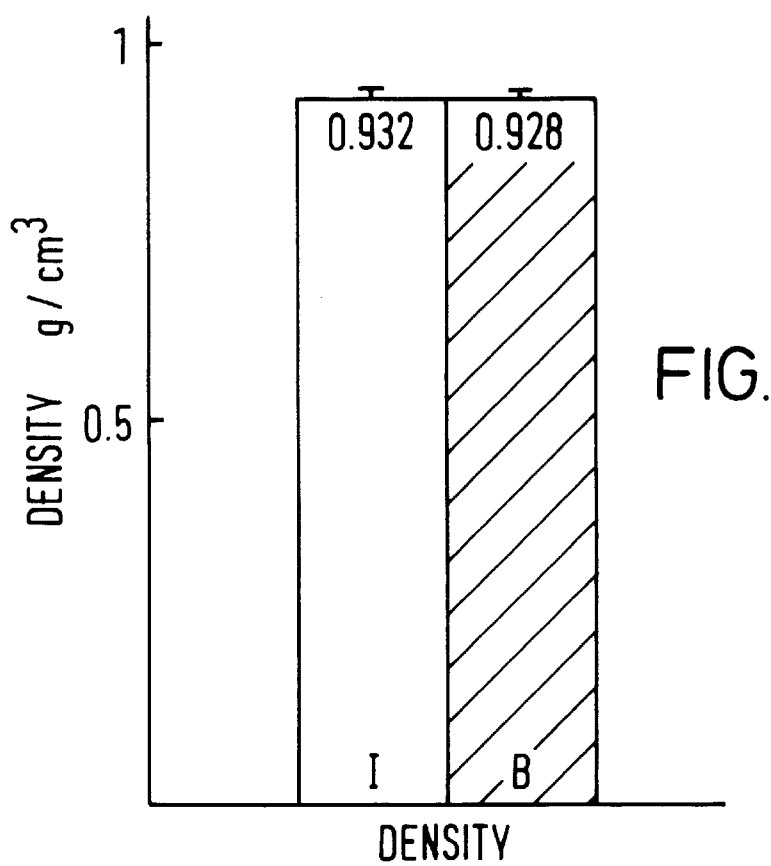
FIG. 6 is a graph showing the relative density of drawn materials (B) which can be used in the bearing elements relative to drawn isotropic source material (I)
Figure 7:
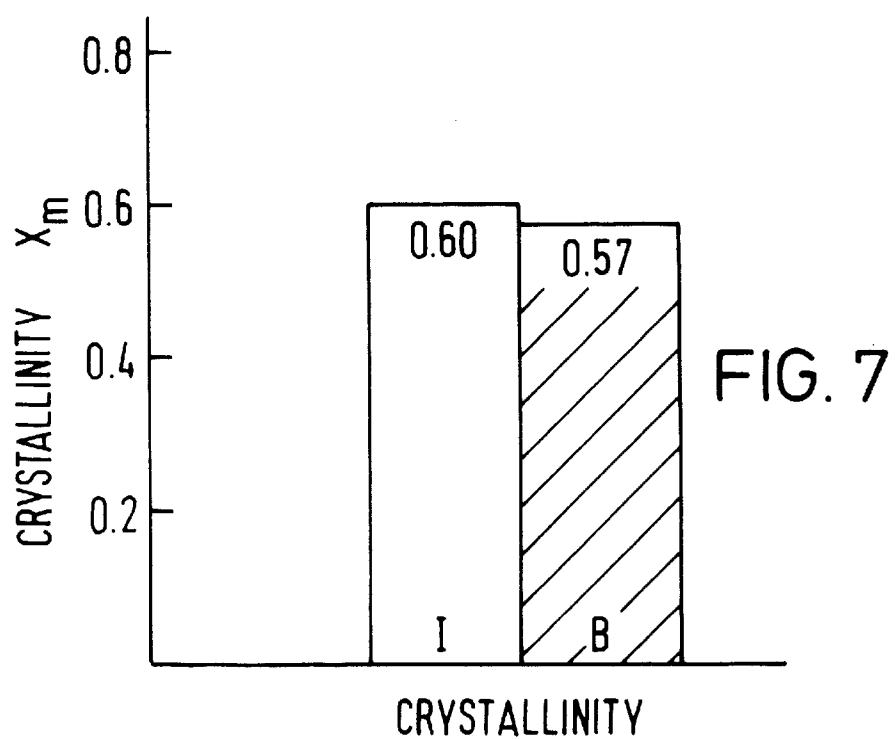
FIG. 7 is a graph showing the relative crystallinity of the material (B) which can be used in the bearing elements relative to isotropic source material (I)

The first method demonstrates die drawing of molecular weight 4.5 million UHMWPE in both uniaxial and biaxial forms. The drawn materials had similar density and crystallinity as shown in FIGS. 6 and 7 to the isotropic source material. The molecular orientation of the drawn material was confirmed by X-ray diffraction.

The material is intended for use as polymer components in artificial joints as set forth above, which undergo complex loading regimes, stress field and wear patterns, it is considered preferable to enhance the properties of the UHMWPE in two directions, by using biaxial drawing methods.

Figure 8:
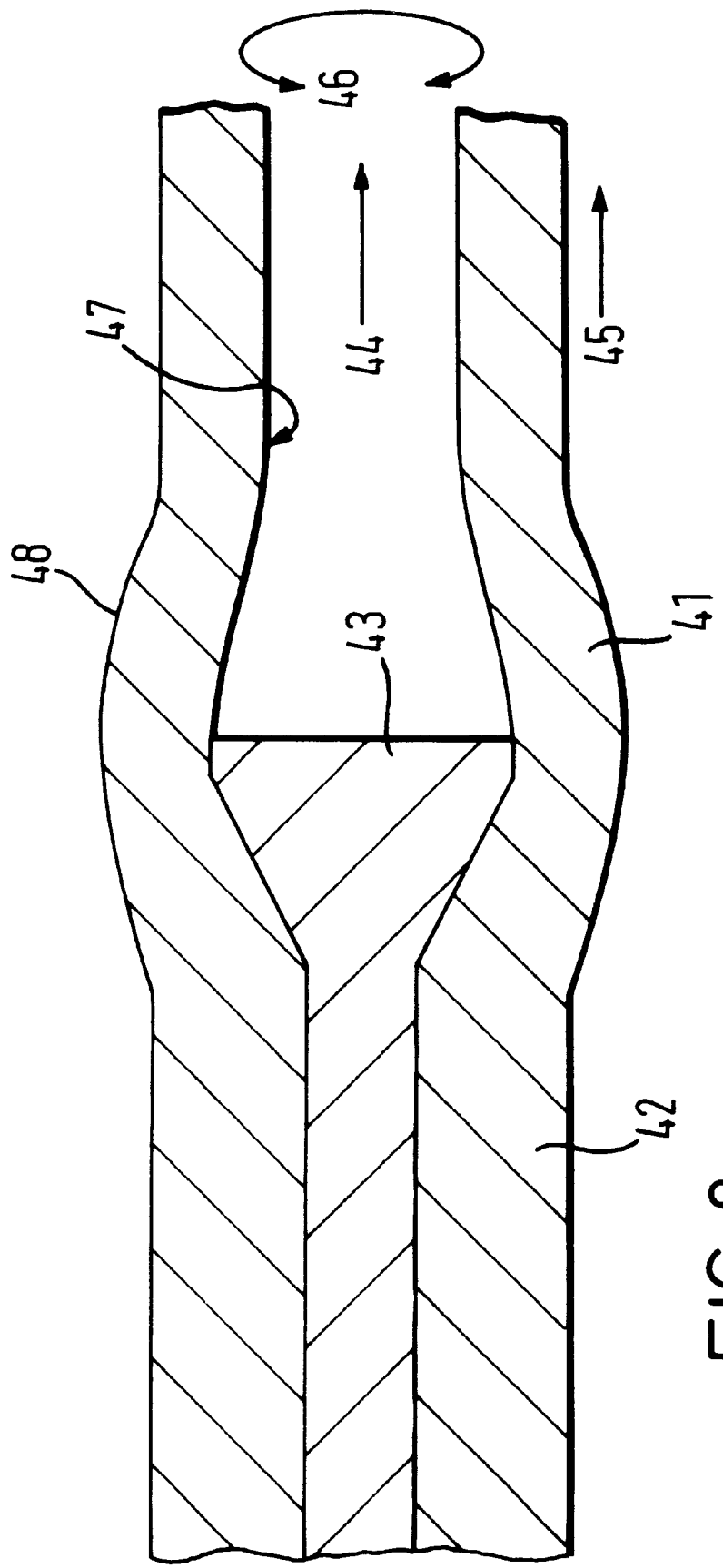
FIG. 8 is a diagrammatic representation of one method used to provide the material for the bearing element.
Figure 9:
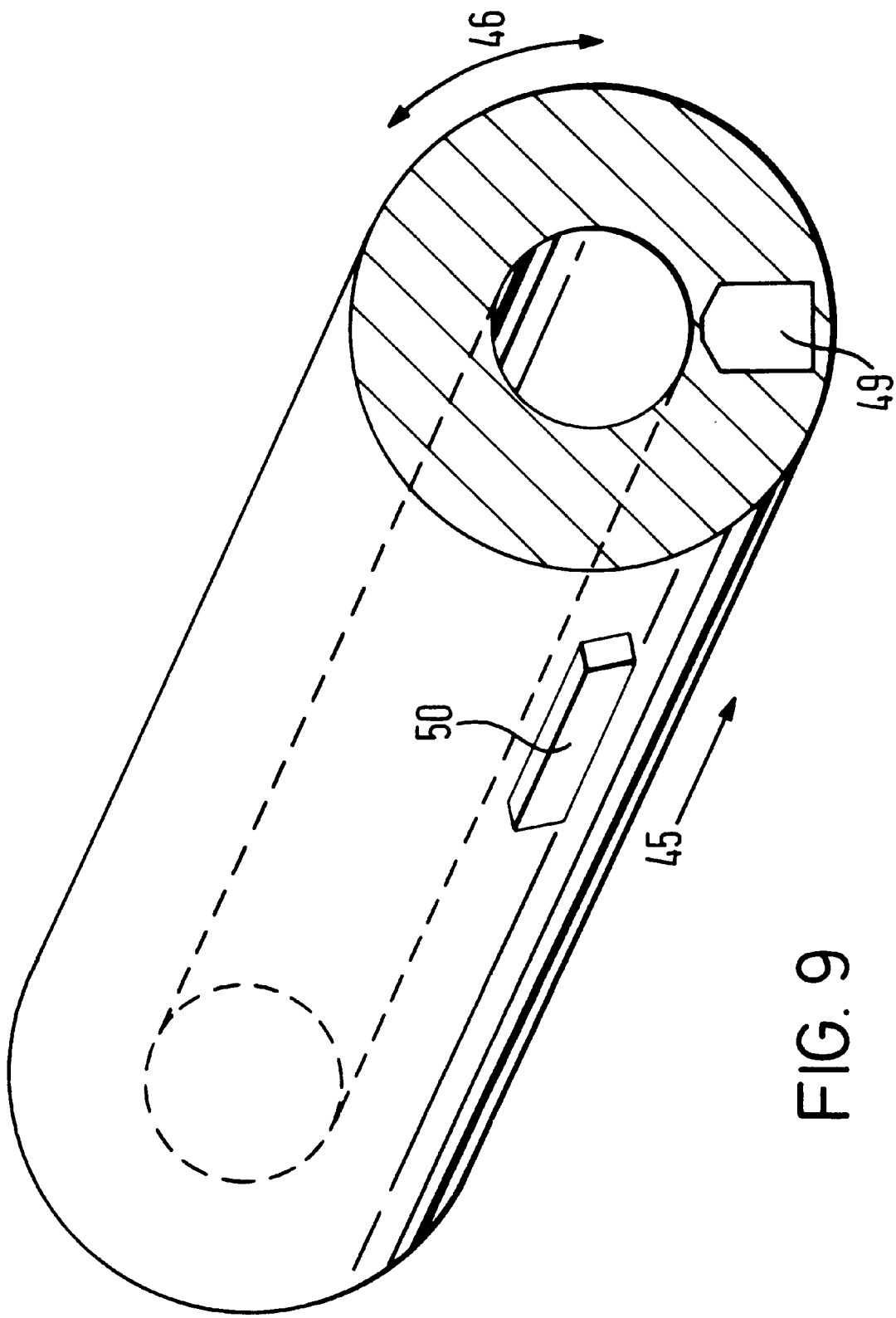
FIG. 9 is a diagrammatic perspective view of a material produced by the method shown in FIG. 3.

FIG. 8 shows a method used for biaxial orientation of a thick walled tube 41, by drawing a material 42 over a mandrel 43 which is of increasing diameter over its length in the direction of draw indicated by reference numeral 44. Such a method of drawing polyethylene material to produce solid phase deformation is described in GB 2 225 551, the teaching of which is incorporated herein, but the effects produced by the present method were unexpected considering the information set out, for example, in the prior art document referred to above. This method produces orientation in both the longitudinal direction indicated by arrow 45 and hoop direction indicated by arrow 46, as shown in FIGS. 8 and 9, with a higher draw deformation ratio and orientation near the internal surface of the tube 47 than the outside 48 in the hoop direction 46.

Material is produced such that the draw ratios close to the internal surface 47 is similar in magnitude in both the hoop 46 and longitudinal direction 45.

Figure 10:
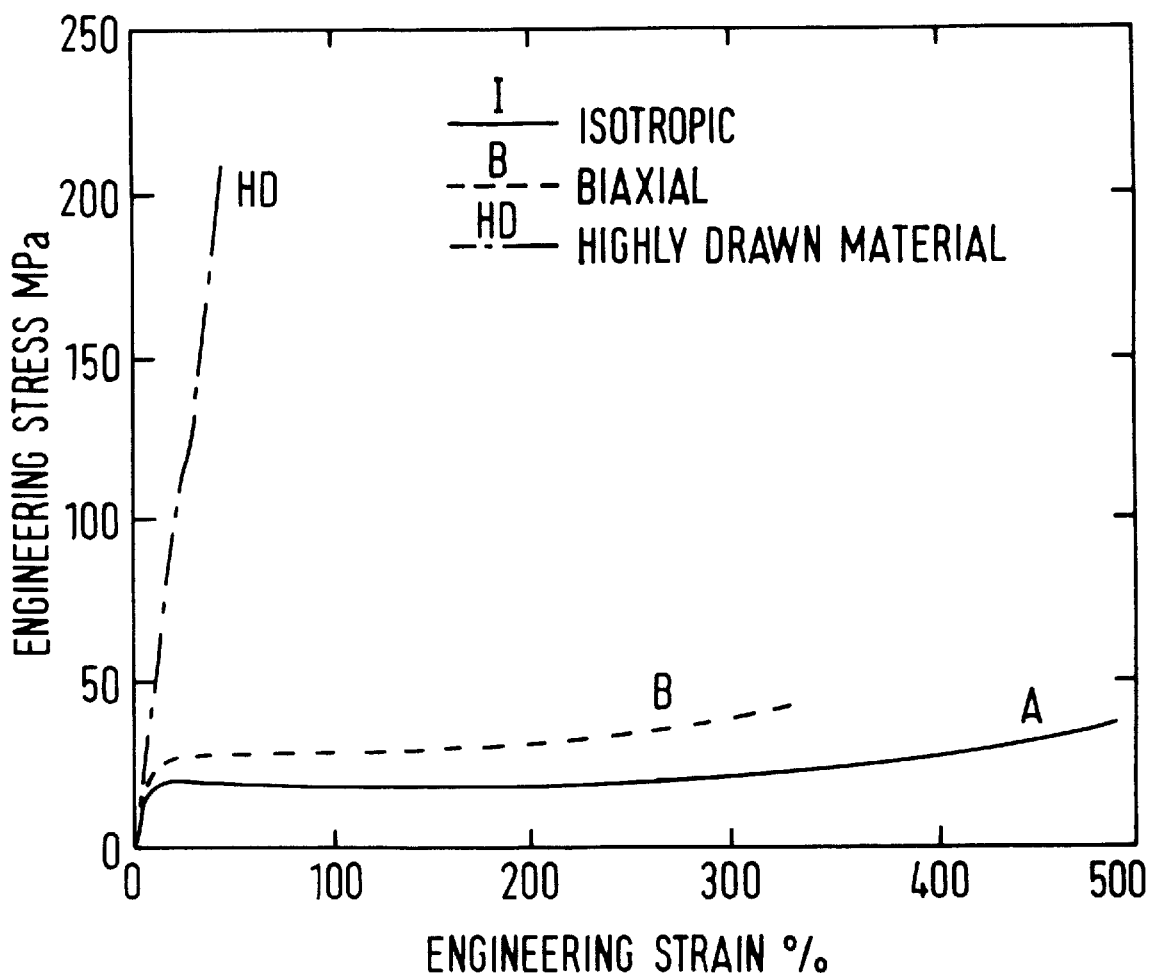
FIG. 10 is a graph showing typical engineering stress strain curves.
Figure 11:
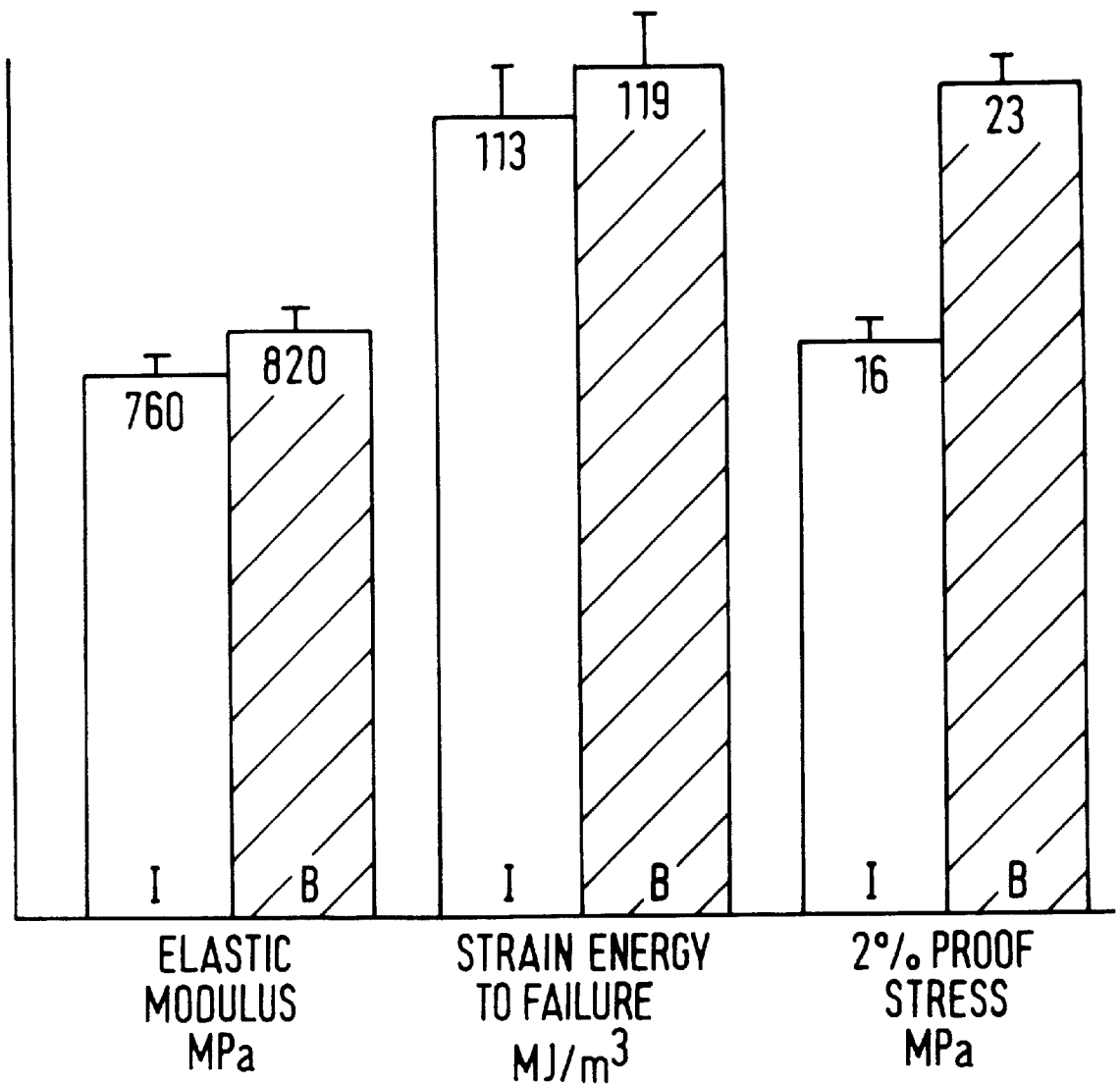
FIG. 11 is a graph showing strain energy to failure and elastic modulus of material made by the method shown in FIG. 3 in comparison with isotropic materials.
Figure 12:
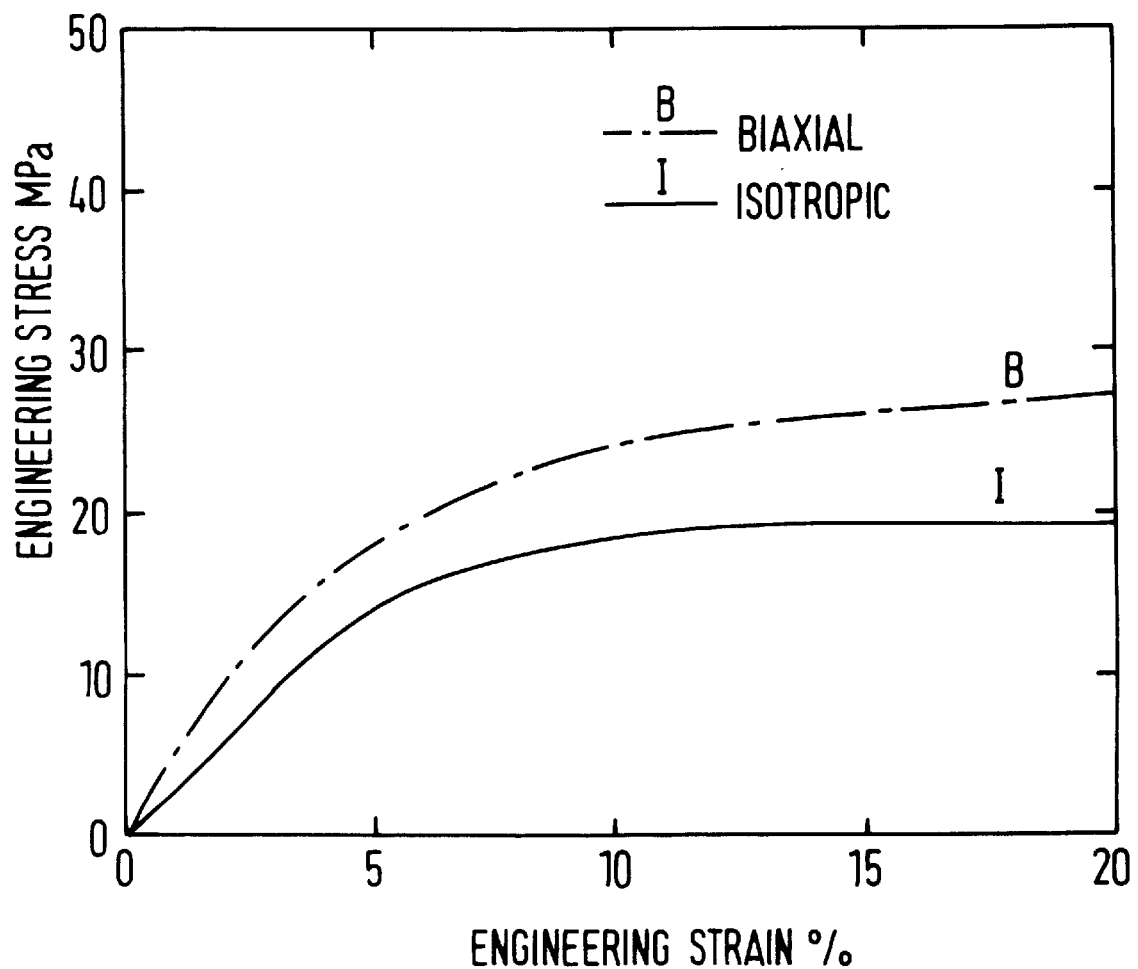
FIG. 12 is a graph showing stress strain curves for materials made by the method described relative to isotropic materials.

FIG. 10 shows typical engineering stress strain curves taken in tension in the longitudinal direction for the isotropic or standard material (A) and biaxially orientated material (B) with a draw ratio of 1.5 in each direction. This shows that the drawn material had a reduction in the strain to failure, approximately similar strain energy to failure and a higher proof stress and working stress range compared to the isotropic material. Increasing the draw ratio further adversely affected both the strain and strain energy to failure, producing a much more brittle material as shown in the curve for the highly drawn uniaxial material with a ratio of 4 to 1 as shown in FIG. 10. Biaxially drawn material with a draw ratio of approximately 1.5 in each direction was considered to produce the most appropriate change in properties with a statistically significant increase in proof stress and working stress range while maintaining a similar strain energy to failure and elastic modulus to the isotropic material as shown in FIG. 11. A detailed examination of the stress strain curve for the two materials at low strains shows clearly the improved characteristics of the biaxially oriented material as shown in FIG. 12.

Seven one meter long length of thick walled tube were produced from three different 75 mm thick slabs of GUR412 UHMWPE. The final dimensions of the drawn tube produced a wall thickness of between 10 and 15 mm with an outside diameter of 63 mm. The drawn material was found to have some dimensional instability when machined components were taken from the drawn tube, due to the release of inbuilt strains.

Two types of wear tests were carried out, a polymer pin on metal reciprocating plate with reciprocating motion, and a spherical ended metal pin on polymer plate under reciprocating motion. The first test configuration may be considered more appropriate for hip joint applications, while the second test may be considered more suited to knee joint applications. The polymer pins and plates were taken with their wear surfaces close to the internal diameter of the drawn tube, where the draw ratio was approximately 1.5 in each direction, such a pin 49 and a plate 50 are shown in FIG. 9. Each test consisted of direct comparison between the biaxial material and the isotropic control material. Tests were carried out for sliding distances greater than 250 km (greater than 10 years equivalent), with more than 15 measurements in each test to allow statistical analysis. Tests were run in bovine serum as a lubricant, and the wear rate was expressed as a normalized wear factor K when, $$\text{Wear factor} = \frac{\text{Wear Volume}}{\text{Load and Sliding Distance}}$$

Figure 13:
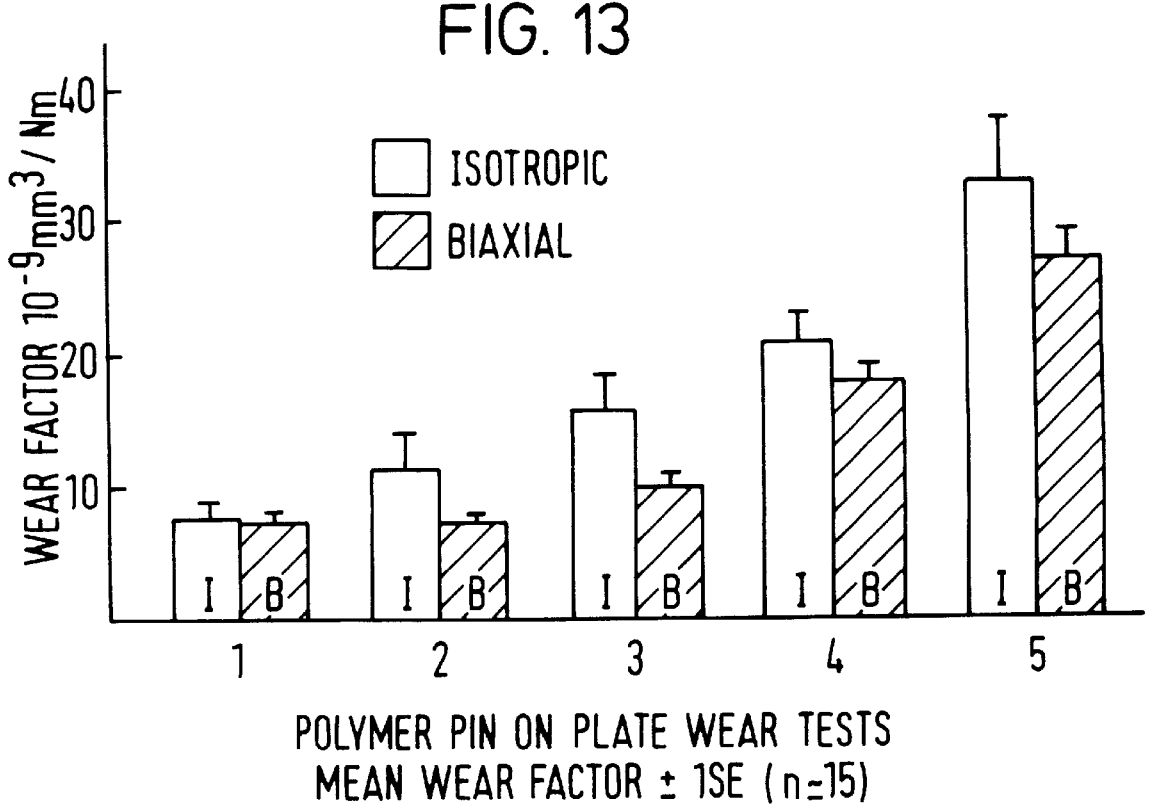
FIG. 13 is a graph showing wear test results.

The results of the five sets of polymer pin 49 on plate tests are shown in FIG. 13. The specific conditions for each of the tests are set out below.

| Polymer Pin on Plate Wear Tests | |
|---|---|
| 1 | 200N Load |
| 2 | 160N Load |
| 3 | 160N Load |
| 4 | 80N Load |
| 5 | 80N Load (rough interface) |

In each of the tests the biaxial material has a lower wear rate than the isotropic control material. The differences were statistically significant at the 20% level in Tests 2 and 3. Overall, the wear factor for the biaxial material was reduced by 22% compared to the isotropic material.

Figure 14:
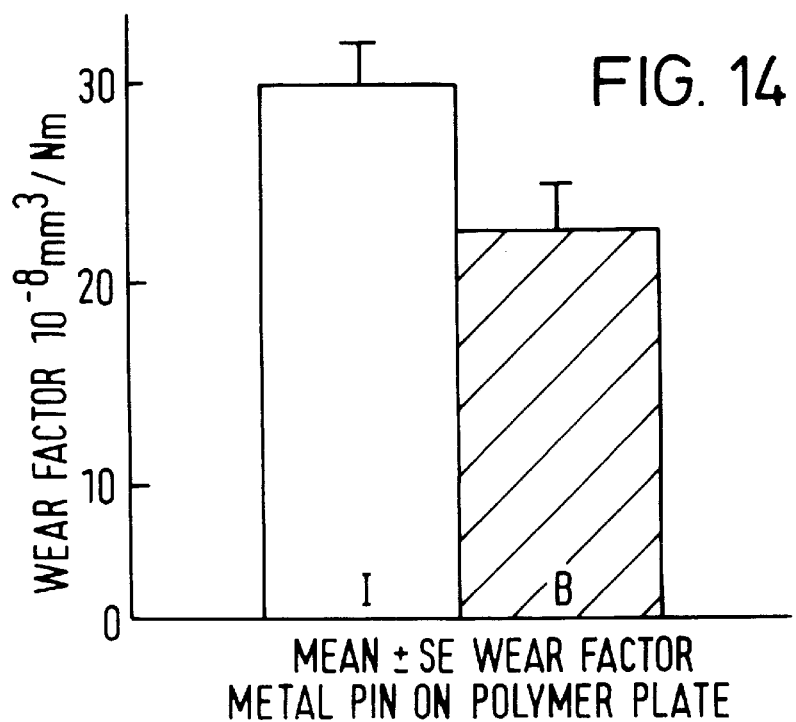
FIG. 14 is another graph showing wear test results.

The results for the polymer plate 50 on a pin test are shown in FIG. 14. The isotropic material showed a higher wear factor than the biaxial material and this was statistically significant at the 5% level. The biaxial drawing of the material was predicted to produce a 25% reduction in the wear rate of this test.

Figure 15:
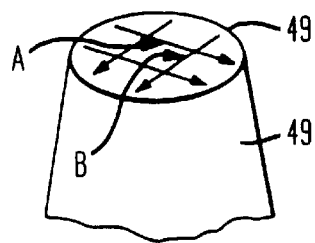
FIG. 15 is a diagrammatic view of a pin used for testing.
Figure 16:
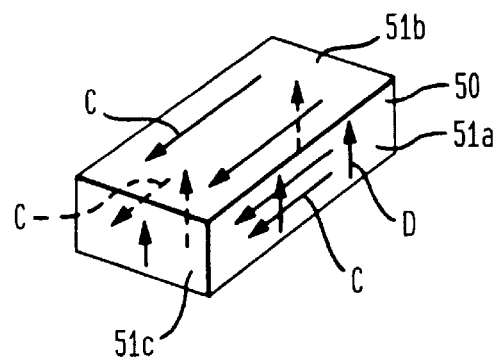
FIG. 16 is a diagrammatic view of a plate used for testing.

FIGS. 15 and 16 are intended to illustrate what is thought to be the lines of molecular orientation on the test pieces. Thus, FIG. 15 shows the work surface 49a on the end of the pin 49. The general direction of the molecular orientation is shown to be in two directions by arrows A and B. The point from which the pin has been taken is shown in FIG. 9 and it will be seen that the lines of orientation are substantially at right angles to each other across the surface.

In FIG. 16 the lines of orientation are again shown in two directions C and D on one face 51a of the plate 50. It will be seen that the lines of orientation are at right angles on this face. On the face 51b however, although the lines of orientation C and D are again at right angles, the lines D exhibit their ends towards the face and on the face 51c the lines of orientation D extend across the face, but the lines C again exhibit their ends.

It will be appreciated that the above Figures only show assumed lines of orientation and are meant to be interpreted in general terms. From the experimental results set forth, it is assumed that the best wear qualities are obtained when the lines are at right angles across the face, as shown in FIG. 15, although this assumption may be only the result of the two different types of experiments applied.

As will be seen from the above, the mechanical properties of ultra high molecular weight polyethylene have been enhanced by biaxial drawing and a significant increase in proof stress and working stress range has been achieved, while maintaining the strain energy to failure. Wear tests have shown that this can produce a 22 to 25% reduction in the wear rate of the biaxially drawn materials compared to the isotropic UHMWPE.

Figure 17:
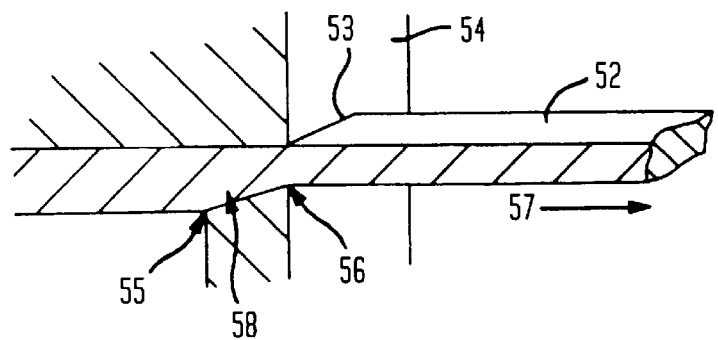
FIG. 17 is a diagrammatic perspective view of another method of making material for the bearing elements.

An alternative method of causing solid phase deformation in at least two directions to UHMWPE can be applied by a slot type drawing method. As shown in FIG. 17, a rectangular or square strip of pre-machined UHMWPE 52 is drawn through a slot 53 of a slot-type die 54 having an entry opening 55 and a discharge opening 56. The direction of draw is indicated by arrow 57 and the transverse width of the slot 53 is equivalent to the transverse width of the strip 52 at entry.

With this arrangement there is solid phase deformation in the draw direction 57 and at an angle thereto, indicated by arrow 58 in the die slot, thus causing solid phase deformation in two directions to cause the preferred multi-axial orientation. The deformation ratios, that is the draw ratio and in effect the compression ratio in the slot, are both between 1.3 to 1.9.

Figure 18:
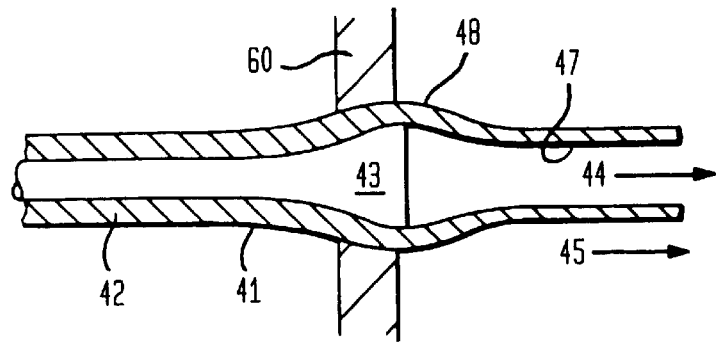
FIG. 18 is a diagrammatic side elevation of a third method of making material for the bearing elements.

FIG. 18 shows a method similar to that described and shown in FIG. 8 and the same reference numerals are used to indicate similar parts but in this method the tube of material also passes through a control die 60.

Other methods of producing solid phase deformation in at least two directions will be apparent to those skilled in the art, for example, rolling and drawing, the governing factor being that the deformation ratios are between 1.3 to 1.9 to produce the preferred multi-axial orientation.

I claim:

1. A prosthetic bearing element having a bearing surface, said bearing surface made from a polyethylene material taken from close to the internal diameter of a drawn polyethylene tube, said tube made from polyethylene having a molecular weight greater than 1,000,000, said tube subjected to a single solid phase deformation in two directions to cause an orientation of the polymeric chains parallel to a bearing surface of said bearing element in only two perpendicular directions in the same area of the bearing surface, said deformation in two directions, having a deformation ratio of 1.3 to 1.9.

2. The prosthetic bearing element as claimed in claim 1 in which said deformation ratios in each direction are 1.5 to 1.6.

3. The prosthetic bearing element as claimed in claim 2 wherein the polyethylene has a molecular weight greater than 4,000,000.

4. The prosthetic bearing element as claimed in claim 1 wherein a first of said two solid phase deformations includes a deformation performed in a lengthwise direction of the tube and a second deformation is performed in a substantially transverse direction thereto.

5. The prosthetic bearing element as claimed in claim 4 in which the second deformation is greater than the first.

6. The prosthetic bearing element as claimed in claim 5 wherein the tube is a hollow tube and passed over a forming die of increasing cross-sectional area, the second deformation taking place in a circumferential direction.

7. The prosthetic bearing element as claimed in claim 6 in which the tube is passed over said forming die without applying an external force to the tube.

8. The prosthetic bearing element as claimed in claim 5 wherein the tube is solid.

9. The prosthetic bearing element as claimed in claim 8 wherein the tube has a square or rectangular cross-section.

10. The prosthetic bearing element as claimed in claim 5 wherein the tube is drawn through a die.

11. The prosthetic bearing element as claimed in claim 5 wherein the tube is passed through a die.

* * * * *

UNITED STATES PATENT AND TRADEMARK OFFICE
CERTIFICATE OF CORRECTION

PATENT NO. : 6,146,426
DATED : November 14, 2000
INVENTOR(S) : Doyle

It is certified that error appears in the above-identified patent and that said Letters Patent is hereby corrected as shown below:

Title page,
In the title, line 1, before "Prosthetic" insert -- A --.

Column 1,
Line 1, before "Prosthetic"" insert -- A --.

Column 6,
Line 35, cancel the ",".
Line 35, cancel "a".
Line 35, "ratio" should read -- ratios --.
Line 44, "a first of said two solid phase deformations" should read -- the deformation --.
Line 45, after "a" (first occurrence) insert -- first --.
Line 46, cancel "is".
Line 50, cancel "a hollow tube and".

Signed and Sealed this

Twenty-third Day of October, 2001

Attest:

NICHOLAS P. GODICI
Attesting Officer   Acting Director of the United States Patent and Trademark Office